United States Patent [19]

Cooper et al.

[11] Patent Number: 4,859,686

[45] Date of Patent: Aug. 22, 1989

[54] DIHYDROPYRIDINE ANTI-ALLERGIC AND ANTI-INFLAMMATORY AGENTS

[75] Inventors: Kelvin Cooper, Deal; John Steele, Sandwich; Kenneth Richardson, Birchington, all of England

[73] Assignee: Pfizer Inc., New York, N.Y.

[21] Appl. No.: 294,322

[22] Filed: Jan. 6, 1989

[30] Foreign Application Priority Data

Feb. 19, 1988 [GB] United Kingdom ................. 8803963

[51] Int. Cl.$^4$ .................... C07D 401/14; A61K 31/41
[52] U.S. Cl. .................................... 514/330; 514/303; 514/340; 546/256; 546/276; 546/119

[58] Field of Search ........................ 546/256, 276, 119; 514/333, 340, 303

[56] References Cited

U.S. PATENT DOCUMENTS 4,515,799  5/1985  Campbell et al. .................... 546/271
4,788,205 11/1988  Cooper et al. ....................... 546/270

Primary Examiner—Jane T. Fan
Attorney, Agent, or Firm—Peter C. Richardson; J. Trevor Lumb; James M. McManus

[57] ABSTRACT

4-Aryl-3-alkoxycarbonyl-6-methyl-5-carbamyl-2-triazolylalkoxymethyl-1,4-dihydropyridines as anti-allergic and anti-inflammatory agents.

7 Claims, No Drawings

DIHYDROPYRIDINE ANTI-ALLERGIC AND ANTI-INFLAMMATORY AGENTS

BACKGROUND OF THE INVENTION

This invention relates to dihydropyridines, specifically to certain 4-aryl-5-carbamoyl-1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF) 1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAC in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute broncho-constriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This, coupled with evidence showing that circulating PAF levels are increased by endotoxin infusion, indicates that PAF is a prime mediator in certain forms of shock. Intravenous infusion of PAF at doses of 20–200 pmol kg$^{-1}$ min$^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

SUMMARY OF THE INVENTION

Thus the compounds of the invention, by virtue of their ability to antagonise the actions of PAF, could well be of value in the treatment of any of the above conditions.

According to the present invention there are provided compounds of the formula

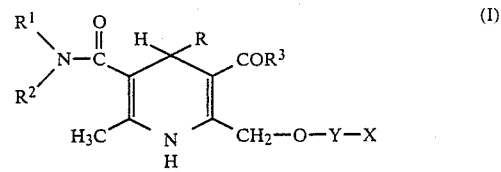

where R is chlorophenyl; $R^1$ is pyridyl or alkyl of one to six carbon atoms; $R^2$ is hydrogen; $R^3$ is alkoxy of one to three carbon atoms; Y is alkylene of two to four carbon atoms; and X is triazolo[2,3-a]pyrid-2-yl or 1,2,4-triazolyl optionally mono or disubstituted by a substituent selected from the group consisting of phenyl and methyl.

A preferred group of compounds are those wherein R is 2-chlorophenyl, $R^1$ is alkyl of one to six carbon atoms, $R^3$ is ethoxy and Y is ethylene. Especially preferred within this group is the compound where $r^1$ is t-butyl and X is 3,5-dimethyl-4H-1,2,4-triazol-4-yl.

A second group of preferred compounds are those wherein R is 2-chlorophenyl, $R^1$ is pyridyl, $R^3$ is ethoxy and Y is ethylene. Especially preferred within this group is the compound where $R^1$ is 2-pyridyl and X is 3,5-dimethyl-4H-1,2,4-triazol-4-yl.

The present invention also includes a method for treating an inflammatory or allergic reaction in a mammal which comprises administering to said mammal an anti-inflammatory or anti-allergic effective amount of a compound of formula (I) and a pharmaceutical composition comprising a unit dosage form of a compound of formula (I) together with a pharmaceutically acceptable diluent or carrier.

The compounds of the formula (I) contain at least one asymmetric centre and exist as one or more pairs of enantiomers. Such pairs or individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compound of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

DETAILED DESCRIPTION OF THE INVENTION

The compounds of formula (I) may be obtained by the Hantzsch synthesis, according to the following reaction scheme:

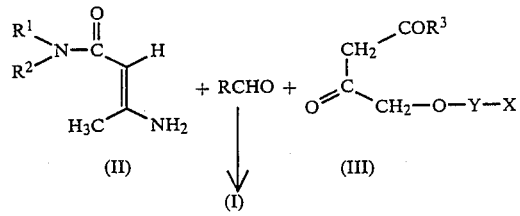

wherein R, $R^1$, $R^2$, $R^3$, Y and X are as previously defined, except that $R^3$ cannot be OH.

In a typical procedure, the ketoester or ketoamide (III) and aldehyde are heated under reflux in a suitable organic solvent, e.g. a $C_1$–$C_4$ alkanol such as ethanol, for about 15 minutes, and then the amino-crotonamide (II) is added. Alternatively the aminocrotonamide (II), the ketoester or ketoamide (III) and the aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by partition, recrystallisation or by chromatography.

Certain compounds of formula (I) are also conveniently obtained by means of simple chemical transformation reactions. Thus for example compounds of formula (I) wherein $R^3$ is benzyloxy may be subjected to a conventional catalytic hydrogenation to yield the corresponding compounds wherein $R^3$ is OH. The acid product may then be reacted with ammonia or with an amine in the presence of a diimide coupling agent, to yield the amide or substituted amide wherein $R^3$ is $NR^4R^5$. Appropriate reagents and conditions for these transformations will be well known to those skilled in the art.

The ketoesters and ketoamides of formula (III) are either known compounds or can be prepared by methods analogous to those of the prior art, such as the method described in European Pat. No. 100189 which is essentially the method of Troostwijk and Kellogg, J.C.S. Chem. Comm., 1977, p. 932, or as described in the Preparations given hereafter. Similarly the aminocrotonamides (II) are either known compounds or can be prepared by conventional procedures, for example from the ketoamide by reaction with ammonia. Also the aldehydes RCHO are either known or can be prepared by known methods in accordance with literature precedents.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated with stirring for two minutes at 37° C. in a Paton aggregometer, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the PAF challenge repeated. The ability of the compound to reduce the bronchoconstrictor effect of PAF is calculated as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic, inflammatory and hypersecretory conditions in a human being.

The preparation of the compounds of the invention is further illustrated by the following Examples.

EXAMPLE 1

4-(2-Chlorophenyl)-3-ethoxycarbonyl-6-methyl-5-(N-pyrid-2-yl-carbamoyl)-2-[2-(3-methyl-5-phenyl-4H-1,2,4-triazol-4-yl)ethoxymethyl]-1,4-dihydropyridine 2-Chlorobenzaldehyde (0.3 g, 2.12 mmole), N-(pyrid-2-yl)-3-aminocrotonamide (0.38 g, 2.12 mmole) (obtained from N-(pyrid-2-yl)-3-oxobutanamide by reaction with ethanolic ammonia at room temperature for 16 hours) and ethyl 4-[2-(3-methyl-5-phenyl-4H-1,2,4-triazol-4-yl)ethoxy]-3-oxobutanoate (0.7 g, 2.12 mmole) were dissolved in absolute ethanol (25 ml) and the mixture heated under reflux for 5 hours. The solution was cooled and concentrated to dryness under reduced pressure. The residue was chromatographed on silica, eluting with ethyl acetate containing 15% ethanol. Appropriate fractions were combined, concentrated under vacuum and the residue triturated with ethyl acetate to yield the title product as a white amorphous solid (0.23 g, 20%), m.p. 167°–169° C. Found: C,64.92; H,5.61; N,13.39. $C_{33}H_{33}ClN_6O_4$ requires C,64.65; H,5.43; N,13.71%.

EXAMPLES 2-6

The following compounds were prepared by the method of Example 1 starting with the appropriate ketoester of formula (III) and reacting with 2-chlorobenzaldehyde and either N-(pyrid-2-yl)-3-aminocrotonamide or N-t-butyl-3-aminocrotonamide:

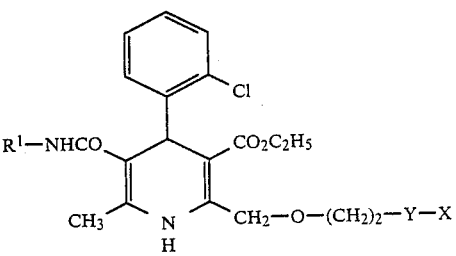

| Example No. | $R^1$ | Y—X | m.p. °C. | Analysis % (Theoretical in brackets) | | |
|---|---|---|---|---|---|---|
| | | | | C | H | N |
| 2 | 2-pyridyl | —(CH₂)₃— pyridazinyl | 152–3 | 63.28 (63.42 | 5.37 5.32 | 14.08 14.32) |
| 3 | 2-pyridyl | —(CH₂)₂—N(3,5-dimethyl-1,2,4-triazol-4-yl) | 203–7 | 60.15 (60.05 | 5.63 5.76 | 14.98 15.00)[1] |
| 4 | $(CH_3)_3C-$ | —(CH₂)₂—N(3,5-dimethyl-1,2,4-triazol-4-yl) | 144–7 | 60.59 (60.66 | 6.85 6.88 | 13.21 13.10)[2] |
| 5 | $(CH_3)_3C-$ | —(CH₂)₂—N(3-methyl-5-phenyl-1,2,4-triazol-4-yl) | 140–3 | 64.73 (64.91 | 6.06 6.47 | 11.85 11.83) |

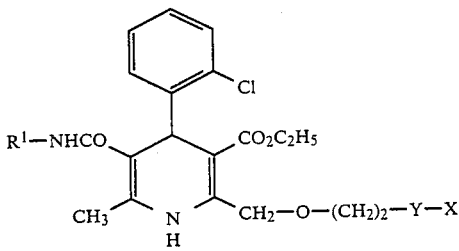

| Example No. | R¹ | Y—X | m.p. °C. | Analysis % (Theoretical in brackets) C | H | N |
|---|---|---|---|---|---|---|
| 6 | pyridin-2-yl | —(CH₂)₃—[1-methyl-tetrazol-5-yl] | 208–213 | 60.67 (61.03 | 5.69 5.67 | 15.06 15.25) |

(1)Hemihydrate
(2)0.25 H₂O

Preparation of Starting Materials

(a) 3,5-Dimethyl-4-(2-hydroxyethyl)-4H-1,2,4-triazole 2,5-Dimethyl-1,3,4-oxadiazole (19.7 g, 0.2 mmole) and ethanolamine (18.3 g, 0.3 mole) were dissolved in 1-methyl-2-pyrrolidinone (20 ml) and the stirred reaction mixture heated at 160° C. for 24 hours, then cooled to ambient temperature. The residual gum was chromatographed on silica eluting with ethyl acetate containing from 20% to 50% methanol. Evaporation of the appropriate fractions and trituration of the residual foam with ethyl acetate gave the title product (14 g, 50%).

(b) 4-(2-Hydroxyethyl)-3-methyl-5-phenyl-4H-1,2,4-triazole

60% Perchloric acid (12 ml) was added to a stirred suspension of 1-acetyl-2-benzoyl hydrazine (31 g, 0.174 mole) in acetic anhydride (150 ml) over 45 minutes at 5°±5° C. The solution was brought to ambient temperature over 1 hour, then filtered. The precipitate was dissolved in water (200 ml), solid sodium carbonate added to pH 9 and the product extracted with ethyl acetate. The extract was washed with water, dried over MgSO₄ and concentrated to an oil. Chromatography gave 2-methyl-5-phenyl-1,3,4-oxadiazole as a gum (9 g, 30%). This was reacted with ethanolamine following the procedure of Preparation (a) above to give the title compound as an oil (5 g).

(c) 3-(3-Hydroxypropyl)-4-methyl-4H-1,2,4-triazole

Sodium methoxide (1.44 g, 21.2 mole) was added to a stirred solution of 1-ethylsuccinyl-4-methyl-3-thiosemicarbazide (4.435 g, 19.25 mmol) (prepared by reaction of 4-methyl-3-thiosemicarbazide and ethyl succinyl chloride in tetrahydrofuran) in absolute ethanol (40 ml). The stirred reaction mixture was heated under reflux for 15 hours. The reaction mixture was cooled, filtered and the filtrate evaporated under reduced pressure to give ethyl-[3-(4- methyl-5-mercapto-4H-1,2,4-triazol-3-yl)]propionate (3.5 g, 86%). This product (9.9 g, 46 mmole) in ethanol (100 ml) was treated with Raney nickel (10 g) and the mixture heated at 80° C. in an autoclave for 15 hours. The reaction mixture was cooled, filtered and the solvent evaporated. Chromatography on silica eluting with 20% methanol in ethyl acetate gave ethyl [3-(4-methy-4H-1,2,4- triazol-3-yl)]propionate as an oil (6.6 g, 78%).

This product (183 mg, 1 mmole) in anhydrous tetrahydrofuran (1 ml) was added dropwise to a stirred suspension of lithium aluminium hydride (40 mg, 1 mmole) in anhydrous tetrahydrofuran (2 ml). The reactants were stirred at ambient temperature for 2 hours then water (0.4 ml) was added, followed by 15% aqueous sodium hydroxide (1.2 ml) and water (0.4 ml). Magnesium sulphate (0.5 g) was then added, the suspension diluted with ethyl acetate (5 ml), stirred for 5 minutes, and filtered. The filtrate was concentrated under vacuum to give the title product as an oil (138 mg, 98%).

(d) Ethyl 4-[2-(3-methyl-5-phenyl-4H-1,2,4-triazol-4-yl)ethoxy]-3-oxobutanoate 4-(2-Hydroxyethyl)-3-methyl-5-phenyl-4H-1,2,4-triazole (4.965 g, 24.4 mmole) was added in one lot to a stirred suspension of sodium hydride (60% dispersion; 2.17 g, 54 mmole) in anhydrous tetrahydrofuran (40 ml). The reaction mixture was placed in an ultrasound bath for 2 hours. Sonication was stopped, the solution cooled to 0° C. and a solution of ethyl-4-chloroacetoacetate (4.02 g, 24.4 mmole) in anhydrous tetrahydrofuran added over 20 minutes at 2°±2° C. The reaction mixture was then replaced in the ultrasound bath and sonication continued for 8 hours. 2N hydrochloric acid (50 ml) was added to the solution, the bulk of the tetrahydrofuran removed under reduced pressure and the residue washed with dichloromethane. Solid sodium bicarbonate was added to the aqueous phase to give pH 8 and the product extracted with ethyl acetate (2×100 ml). The organic extracts were dried over magnesium sulphate and the residue flash chromatographed on silica eluting with 15% methanol in ethyl acetate. The appropriate fractions were combined and concentrated to give the title keto ester as an oil (4.71 g, 60%). N.m.r. (δ, CDCL₃): 1.28 (t, J=8 Hz, 3H), 2.58 (s, 3H), 3.34 (s, 2H), 3.65 (t, J=6.5 Hz, 2H), 4.08 (s, 2H), 4.21 (m, 4H), 7.52 (m, 3H) and 7.64 (m, 2H).

The following keto esters of formula (III) were made by the method of Preparation (d) above, using the appropriate alcohol starting material:

| $C_2H_5O_2C-CH_2-CO-CH_2-O-Y-X$ | |
|---|---|
| Y—X | N.m.r. (CDCl₃) |
| -(CH₂)₃-[1,2,4-triazolo-pyridazine] | 1.28 (t, J = 6Hz, 3H); 2.22 (m, 2H); 3.05 (t, J = 6Hz, 2H); 3.57 (s, 2H); 3.63 (t, J = 3Hz, 2H); 4.12 (s, 3H); 4.20 (q, J = 6Hz, 2H); 6.99 (m, 1H); 7.51 (m, 1H); 7.64 (d, J = 5Hz, 1H); 8.54 (d, J = 5Hz, 1H). |
| -(CH₂)₂-N[3,5-dimethyl-1,2,4-triazolyl] | 1.31 (t, J = 8Hz, 3H); 2.46 (s, 3H); 3.42 (s, 2H); 3.74 and 4.06 (each t, J = 6Hz, 2H); 4.20 (q, J = 8Hz, 2H). |
| -(CH₂)₃-N[1-methyl-1,2,4-triazolyl] | 1.30 (t, J = 7.5 Hz, 3H); 2.15 (m, 2H); 2.87 (t, J = 6.5 Hz, 2H); 3.49 (s, 2H); 3.63 (m, 5H); 4.12 (s, 2H); 4.19 (q, J = 7.5 Hz, 2H); 8.08 (s, 1H). |

We claim:

1. A compound having the formula:-

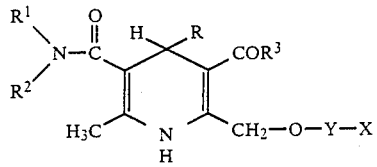

or a pharmaceutically acceptable salt thereof, wherein R is chlorophenyl; $R^1$ is pyridyl or alkyl having one to six carbon atoms; $R_2$ is hydrogen; $R_3$ is alkoxy having one to three carbon atoms; Y is alkylene having two to four carbon atoms; and X is triazolo[2,3-a]pyrid-2-yl or 1,2,4-triazolyl optionally monosubstituted or disubstituted by a substituent selected from methyl or phenyl.

2. A compound of claim 1, wherein R is 2-chlorophenyl, $R^1$ is alkyl having one to six carbon atoms, $R_3$ is ethoxy and Y is ethylene.

3. The compound of claim 2, wherein $R^1$ is t-butyl and X is 3,5-dimethyl-4H-1,2,4-triazol-4-yl.

4. A compound of claim 1, wherein R is 2-chlorophenyl, $R^1$ is pyridyl, $R^3$ is ethoxy and Y is ethylene.

5. The compound of claim 4, wherein $R^1$ is 2-pyridyl and X is 3,5-dimethyl-4H-1,2,4-triazol-4-yl.

6. A method for treating an inflammatory or allergic reaction in a mammal which comprises administering to said mammal an anti-inflammatory or anti-allergic effective amount of a compound according to claim 1.

7. A pharmaceutical composition comprising a unit dosage form of a compound according to claim 1 together with a pharmaceutically acceptable diluent or carrier.

* * * * *